United States Patent
Kodama et al.

(10) Patent No.: US 9,311,826 B2
(45) Date of Patent: Apr. 12, 2016

(54) ENERGY CONSUMPTION ESTIMATOR

(71) Applicant: Tanita Corporation, Itabashi-ku (JP)

(72) Inventors: Miyuki Kodama, Itabashi-ku (JP); Ayumi Sano, Saitama (JP); Atsuo Kumekawa, Itabashi-ku (JP)

(73) Assignee: TANITA CORPORATION, Tokyo (JP)

(*) Notice: Subject to any disclaimer, the term of this patent is extended or adjusted under 35 U.S.C. 154(b) by 233 days.

(21) Appl. No.: 13/828,359

(22) Filed: Mar. 14, 2013

(65) Prior Publication Data

US 2014/0045150 A1 Feb. 13, 2014

(30) Foreign Application Priority Data

Aug. 9, 2012 (JP) ................................. 2012-177261

(51) Int. Cl.
| | |
|---|---|
| *A61B 5/083* | (2006.01) |
| *G09B 19/00* | (2006.01) |
| *A61B 5/11* | (2006.01) |
| *A61B 5/00* | (2006.01) |
| *G01N 33/497* | (2006.01) |

(52) U.S. Cl.
CPC ............ *G09B 19/0092* (2013.01); *A61B 5/083* (2013.01); *A61B 5/11* (2013.01); *A61B 5/1118* (2013.01); *A61B 5/4866* (2013.01); *A61B 5/7278* (2013.01); *G01N 33/497* (2013.01)

(58) Field of Classification Search
CPC .... A61B 5/083; A61B 5/0833; A61B 5/0836; A61B 5/097; A61B 5/11; G01N 33/497
See application file for complete search history.

(56) References Cited

U.S. PATENT DOCUMENTS

2004/0186390 A1* 9/2004 Ross et al. .................... 600/532

FOREIGN PATENT DOCUMENTS

| JP | 2007-089699 A | 4/2007 |
|---|---|---|
| WO | 01/39089 A1 | 5/2001 |
| WO | 01/93743 A2 | 12/2001 |
| WO | WO 0193743 A2 * | 12/2001 |
| WO | 02/05702 A2 | 1/2002 |
| WO | WO 2013019843 A2 * | 2/2013 |

OTHER PUBLICATIONS

"Dietary Reference Intakes for Energy, Carbohydrate, Fiber, Fat, Fatty Acids, Cholesterol, Protein, and Amino Acids," Institute of Medicine, https://www.iom.edu/Reports/2002/Dietary-Reference-Intakes-for-Energy-Carbohydrate-Fiber-Fat-Fatty-Acids-Cholesterol-Protein-and-Amino-Acids.aspx, Sep. 5, 2002.*

(Continued)

*Primary Examiner* — Robert J Utama
*Assistant Examiner* — Jennifer Fassett
(74) *Attorney, Agent, or Firm* — Buchanan Ingersoll & Rooney PC

(57) ABSTRACT

An energy consumption estimator includes a body motion sensor, a first calculation unit, an acquisition unit, and a second calculation unit. The body motion sensor detects body motion by a user. Based on the body motion detected by the body motion sensor, the first calculation unit calculates the user's total energy consumption. The acquisition unit acquires the user's energy consumption derived from fats and lipids. Based on the energy consumption derived from fats and lipids and on the total energy consumption, the second calculation unit calculates the user's total energy derived from carbohydrates.

10 Claims, 9 Drawing Sheets

(56) References Cited

OTHER PUBLICATIONS

"Dietary Guidelines for Americans, 2005," National Resource Center on Nutrition, Physical Activity, and Aging at Florida International University, https://web.archive.org/web/20081203143344/http://www.health.gov/dietaryguidelines/dga2005/toolkit/Providers/Part2.htm, 2005.*

Extended European Search Report dated Dec. 2, 2013, issued by the European Patent Office in corresponding European Application No. 13173427.9. (6 pages).

Office Action issued on Sep. 22, 2015 by the European Patent Office in corresponding European Patent Application No. 13 173 427.9 (5 pages).

* cited by examiner

ENERGY CONSUMPTION ESTIMATOR

CROSS REFERENCE TO RELATED APPLICATION

This application is based on an application No. 2012-177261 filed in Japan on Aug. 9, 2012, the contents of which are hereby incorporated by reference.

TECHNICAL FIELD

The present invention relates to an energy consumption estimator for estimating energy consumed by a user.

BACKGROUND ART

Knowing how much energy one has consumed is crucial for personal weight control, health management, and other such areas. To this end, an activity monitor for measuring the amount of energy one has consumed has been proposed (see Patent Literature 1).

CITATION LIST

Patent Literature

PTL 1: JP2007089699A

SUMMARY OF INVENTION

For areas such as personal weight control and health management, it is important to know not only the total energy consumption, but also the amounts of energy consumption derived respectively from consumed carbohydrates, and fats and lipids. The activity monitor proposed in Patent Literature 1, however, cannot measure the energy consumption derived from carbohydrates.

Accordingly, the present invention has been conceived in light of the above problem, and it is an object thereof to provide an energy consumption estimator that calculates the energy consumption derived from carbohydrates consumed by a user.

In order to solve the above problems, an energy consumption estimator according to the present invention comprises a total energy consumption acquisition unit configured to acquire a total energy consumption for a user; a fat and lipid energy consumption acquisition unit configured to acquire an energy consumption derived from fats and lipids for the user; and a carbohydrate energy calculation unit configured to calculate an energy consumption derived from carbohydrates for the user based on the total energy consumption acquired by the total energy consumption acquisition unit and the energy consumption derived from fats and lipids acquired by the fat and lipid energy consumption acquisition unit.

The energy consumption estimator of the present invention may further comprise a first storage unit configured to store a relationship between total energy in food and energy consumption derived from carbohydrates; and a total energy calculation unit configured to calculate a total energy in food ingested by the user based on the energy consumption derived from carbohydrates calculated by the carbohydrate energy calculation unit and on the relationship stored in the first storage unit.

In the energy consumption estimator of the present invention, based on the total energy consumption from an initial reference time until a measurement reference time, the carbohydrate energy calculation unit may calculate the energy consumption derived from carbohydrates ingested by the user near the initial reference time.

The energy consumption estimator of the present invention may further comprise a timer configured to measure time; a second storage unit configured to store the total energy consumption acquired by the total energy consumption acquisition unit in association with the time measured by the timer; and an input unit configured to detect input of the initial reference time and the measurement reference time, wherein the total energy consumption acquisition unit reads the total energy consumption at the initial reference time detected by the input unit from the second storage unit, acquires the total energy consumption at the measurement reference time, and calculates the total energy consumption from the initial reference time until the measurement reference time by subtracting the total energy consumption at the measurement reference time from the total energy consumption at the initial reference time.

The energy consumption estimator of the present invention may further comprise an input unit configured to detect input of a reset of the total energy consumption acquired by the total energy consumption acquisition unit, wherein the carbohydrate energy calculation unit uses the total energy consumption calculated subsequent to detection of the input of the reset as the total energy consumption from the initial reference time until the measurement reference time.

In the energy consumption estimator of the present invention, the fat and lipid energy consumption acquisition unit may include an acetone detection unit configured to detect an amount of acetone released by the user and a fat and lipid energy consumption calculation unit configured to calculate the energy consumption derived from fats and lipids for the user based on the amount of acetone detected by the acetone detection unit.

In the energy consumption estimator of the present invention, the fat and lipid energy acquisition unit may acquire the energy consumption derived from fats and lipids for the user from an acetone detector that detects an amount of acetone released by the user and that calculates the energy consumption derived from fats and lipids for the user based on the detected amount of acetone.

In the energy consumption estimator of the present invention, the fat and lipid energy acquisition unit may acquire, from an acetone detector that detects an amount of acetone released by the user, the amount of acetone of the user and calculate the energy consumption derived from fats and lipids for the user based on the acquired amount of acetone.

In the energy consumption estimator of the present invention, the total energy consumption acquisition unit may include a body motion sensor configured to detect body motion by the user and a total energy consumption calculation unit configured to calculate the total energy consumption for the user based on the body motion detected by the body motion sensor.

While the solution to the problem by the present invention has been described above in terms of devices, the present invention may also be achieved by a method or a program substantially equivalent to the above devices, or by a storage medium having such a program recorded thereon. These aspects are also to be understood as included in the scope of the present invention.

According to the present invention, the energy consumption estimator having the above structure can calculate the energy consumption derived from carbohydrates consumed by the user.

BRIEF DESCRIPTION OF DRAWINGS

The present invention will be further described below with reference to the accompanying drawings, wherein: to FIG. 1 is an external perspective view of an energy consumption estimator according to Embodiment 1 of the present invention.

DESCRIPTION OF EMBODIMENTS

Figure 1:
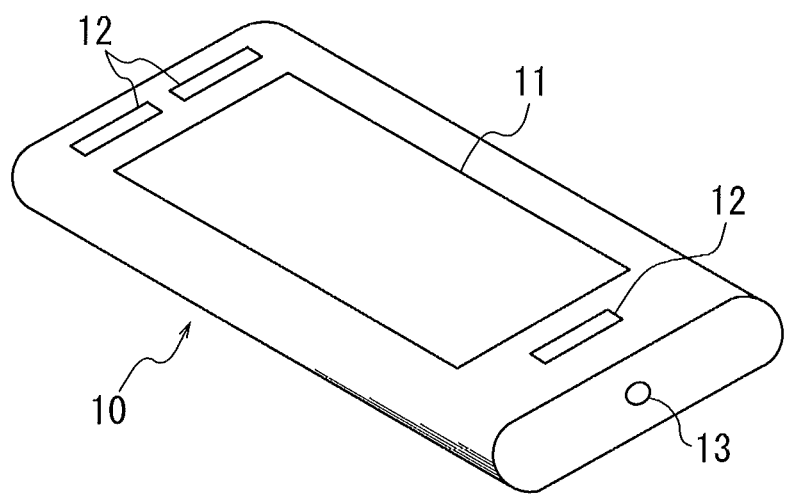

With reference to the drawings, the following describes embodiments of a notification system in which the present invention has been adopted. FIG. 1 is an external perspective view of an energy consumption estimator according to Embodiment 1 of the present invention.

The energy consumption estimator 10 is, for example, an activity monitor that calculates the total energy consumed by a user, as described below. A display 11 and a plurality of buttons 12 are provided on the front of the energy consumption estimator 10. An acetone measurement unit 13 (acetone detection circuitry) is provided on the side of the energy consumption estimator 10.

The display 11 can display a variety of images.

The plurality of buttons 12 allow for detection of input to switch power to the energy consumption estimator 10 on/off, input to switch the operation mode, and a variety of input on a setting screen.

The acetone measurement unit 13 detects the amount of acetone included in the user's breath. Note that in the present embodiment, the acetone measurement unit 13 detects the amount of acetone included in breath, but alternatively the acetone measurement unit 13 may detect the amount of acetone that transpires through the skin.

Figure 2:
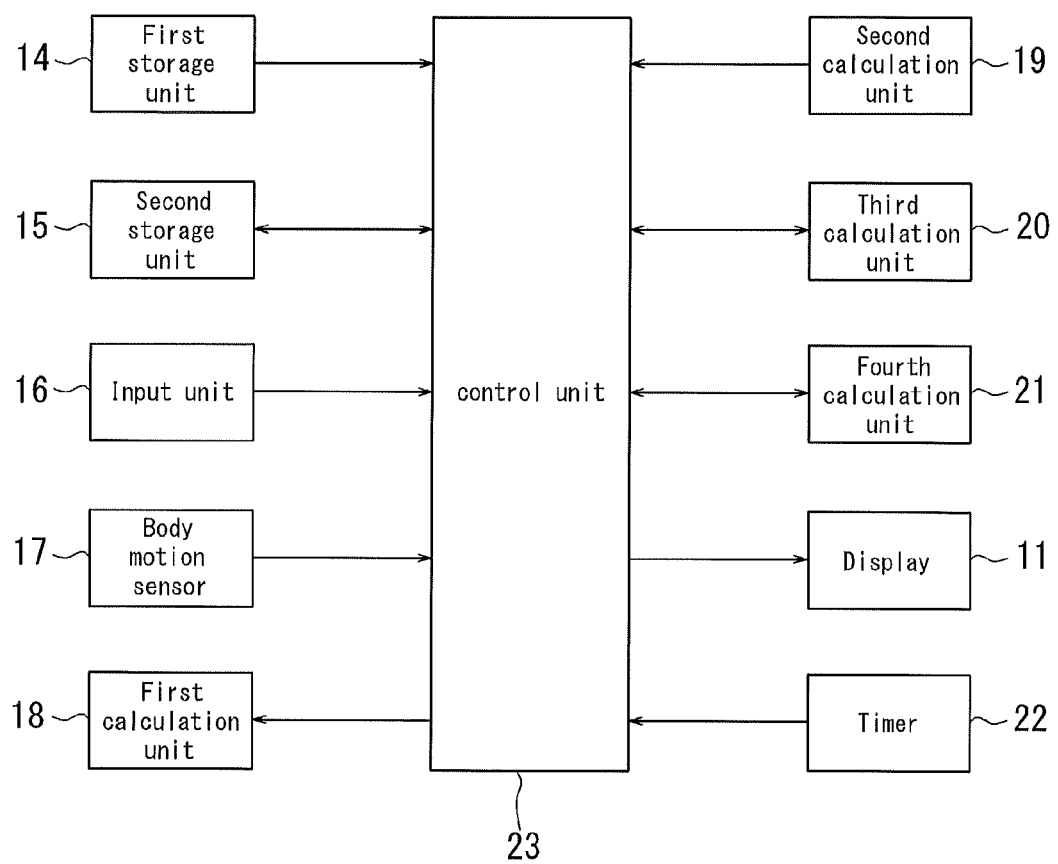
FIG. 2 is a functional block diagram schematically illustrating the internal structure of the energy consumption estimator in FIG. 1.

Next, the internal structure of the energy consumption estimator 10 is described with reference to the functional block diagram in FIG. 2. The energy consumption estimator 10 includes a first storage unit 14 (first storage circuitry), a second storage unit 15 (second storage circuitry), an input unit 16 (input circuitry), a body motion sensor 17, a first calculation unit 18 (total energy consumption calculation circuitry), a second calculation unit 19 (carbohydrate energy calculation circuitry), a third calculation unit 20 (total energy calculation circuitry), a fourth calculation unit 21 (fat energy consumption calculation circuitry), the display 11, a timer 22, and a control unit 23 (comparison circuitry). The body motion sensor 17 and the first calculation unit 18 correspond to claimed total energy consumption acquisition circuitry. The acetone measurement unit 13 and the fourth calculation unit 21 correspond to claimed fat energy consumption acquisition circuitry.

The first storage unit 14 is, for example, EEPROM (Electrically Erasable Programmable Read-Only Memory) storing predetermined information necessary for execution of a variety of functions by the energy consumption estimator 10. For example, the first storage unit 14 stores the relationship between total energy and carbohydrate energy in advance. Note that the relationship between total energy and carbohydrate energy is the relationship, such as the ratio, between the total energy and the carbohydrate energy in food that is ingested in a typical meal. This relationship is statistically determined in advance by gender and age group.

The second storage unit 15 is, for example, SDRAM (Synchronous Dynamic Random Access Memory) and stores the user's personal information detected by the input unit 16, the total energy consumption calculated by the first calculation unit 18, and the total energy derived from fats and lipids detected by the fourth calculation unit 21 as the total energy derived from fats and lipids before a meal, as described below. These values are overwritten or deleted as necessary, as also described below.

The input unit 16 includes the plurality of buttons 12. As described below, the energy consumption estimator 10 includes a plurality of operation modes. The input unit 16 detects input in response to user operation in each operation mode.

As described below, the input unit 16 detects input of the user's personal information, such as the user's age, gender, height, weight, and body fat percentage. As also described below, the input unit 16 detects input to reset the total energy consumption calculated by the first calculation unit 18. The input unit 16 also detects an instruction to switch the operation mode. Furthermore, the input unit 16 detects input indicating fat and lipid consumption measurement. The input unit 16 also detects input selecting whether detection of the amount of acetone is before a meal or not before a meal. Finally, the input unit 16 detects input indicating calculation of the total energy in food.

The body motion sensor 17 is, for example, a tri-axis acceleration sensor module and detects acceleration of the energy consumption estimator 10 in three orthogonal directions. Note that the user wears the energy consumption estimator 10, and therefore the acceleration in three directions of the energy consumption estimator 10 is detected as body motion of the user in three directions.

The first calculation unit 18 calculates the user's total energy consumption based on the user's personal information read from the second storage unit 15 and on the acceleration in three directions detected by the body motion sensor 17. Note that an instantaneous value of the total energy consumption is calculated using a well-known calculation method based on acceleration in three directions and on the user's personal information. The first calculation unit 18 calculates the instantaneous value every minute, for example, and adds up the calculated instantaneous values to calculate the total energy consumption.

When the input unit 16 detects input of a reset, the first calculation unit 18 resets the total energy consumption to zero and again starts calculating the total energy consumption from the reset. In other words, the total energy consumption calculated by the first calculation unit 18 represents the user's total energy consumption from the time of reset (initial reference time) until the present (measurement reference time).

The second calculation unit 19 calculates the energy consumption derived from carbohydrates by subtracting the user's energy consumption derived from fats and lipids, calculated by the fourth calculation unit 21, described below, from the total energy consumption calculated by the first calculation unit 18. Note that, as described below, the energy consumption derived from carbohydrates is calculated by the second calculation unit 19 based on a specific usage method of the energy consumption estimator 10, and thus the energy consumption is equivalent to the carbohydrate energy in food ingested by the user near the reset time. In other words, the second calculation unit 19 estimates the carbohydrate energy in food ingested by the user near the reset time.

The third calculation unit 20 reads the user's personal information from the second storage unit 15. Furthermore, from the first storage unit 14, the third calculation unit 20 reads the relationship between total energy and carbohydrate energy corresponding to the personal information. The third calculation unit 20 also calculates the total energy in ingested food based on the carbohydrate energy calculated by the second calculation unit 19 and the relationship between total energy and carbohydrate energy read from the first storage unit 14.

Based on the amount of breath acetone detected by the acetone measurement unit 13, the fourth calculation unit 21 calculates the user's energy consumption derived from fats and lipids. Note that the amount of acetone released from within the body varies depending on the amount of energy consumption derived from fats and lipids. In other words, the amount of acetone varies depending on the amount of energy from fats and lipids that is burned between when fats and lipids begins to be burned and when the amount of acetone is detected. Based on this principle, the fourth calculation unit 21 calculates the energy consumption derived from fats and lipids.

The display 11 is, for example, a liquid crystal monitor and can display a wide variety of images, as described above.

The timer 22 measures time.

The control unit 23 controls the exchange of information between, and the transmission of instructions to, the first storage unit 14, the second storage unit 15, the input unit 16, the body motion sensor 17, the first calculation unit 18, the second calculation unit 19, the third calculation unit 20, the fourth calculation unit 21, the display 11, and the timer 22, as well as operations by these components.

Next, the functions executed in each of the operation modes of the energy consumption estimator 10 are described in detail. The operation modes of the energy consumption estimator 10 are a setting mode and a measurement mode.

In the setting mode of the energy consumption estimator 10, the user can enter his or her own personal information. When the operation mode is the setting mode, a personal information input image is displayed on the display 11. The input unit 16 detects input during display of the personal information input image as the user's personal information and stores the personal information in the second storage unit 15.

In the measurement mode of the energy consumption estimator 10, calculation of the user's total energy consumption, estimation of the carbohydrate energy in ingested food, and estimation of the total energy in ingested food can be performed. When the operation mode is the measurement mode, the user's total energy consumption calculated by the first calculation unit 18 is stored at each point in time in the second storage unit 15. Note that the points in time are identified based on measurement by the timer 22. The stored total energy consumption can be displayed as a bar graph over these points in time or as a numerical value.

When the input unit 16 detects a reset of the total energy consumption during operation in the measurement mode, the first calculation unit 18 resets the calculated total energy consumption to zero. After resetting the value to zero, the first calculation unit 18 again begins to calculate the total energy consumption.

When the input unit 16 detects input indicating fat and lipid consumption measurement during operation in the measurement mode, the acetone measurement unit 13 and the fourth calculation unit 21 cooperate to acquire the user's energy consumption derived from fats and lipids.

Upon acquisition of the energy consumption derived from fats and lipids, an image requesting selection of whether detection is before a meal or not before a meal is displayed on the display 11.

Upon detection of input selecting detection before a meal, the energy consumption derived from fats and lipids calculated by the fourth calculation unit 21 is stored in the second storage unit 15 as the energy consumption derived from fats and lipids before a meal. As described next, the energy consumption derived from fats and lipids stored in the second storage unit 15 is used for determining whether the energy consumption derived from carbohydrates calculated by the second calculation unit 19 is equivalent to the carbohydrate energy in food ingested near the reset time.

Upon detection of input selecting detection that is not before a meal, the second calculation unit 19 calculates the energy consumption derived from carbohydrates by subtracting the energy consumption derived from fats and lipids calculated by the fourth calculation unit 21 from the total energy consumption calculated by the first calculation unit 18. Furthermore, upon detection of input selecting detection that is not before a meal, the second calculation unit 19 compares the energy consumption derived from fats and lipids calculated by the fourth calculation unit 21 with the energy consumption derived from fats and lipids stored in the second storage unit 15. Based on the comparison, it is determined whether the energy consumption derived from carbohydrates calculated by the second calculation unit 19 is equivalent to the carbohydrate energy in food ingested near the reset time.

When it is determined that the energy consumption derived from carbohydrates calculated by the second calculation unit 19 is not equivalent to the carbohydrate energy in food ingested near the reset time, the message "You are still consuming carbohydrate energy in the food you ate" is displayed on the display 11. The total energy consumption and the energy consumption derived from fats and lipids after the most recent meal, respectively calculated by the first calculation unit 18 and the fourth calculation unit 21, are also displayed on the display 11. Furthermore, the energy consumption derived from carbohydrates calculated by the second calculation unit 19 is displayed on the display 11 as energy consumption derived from carbohydrates for a user who is currently burning carbohydrates.

Figure 3:
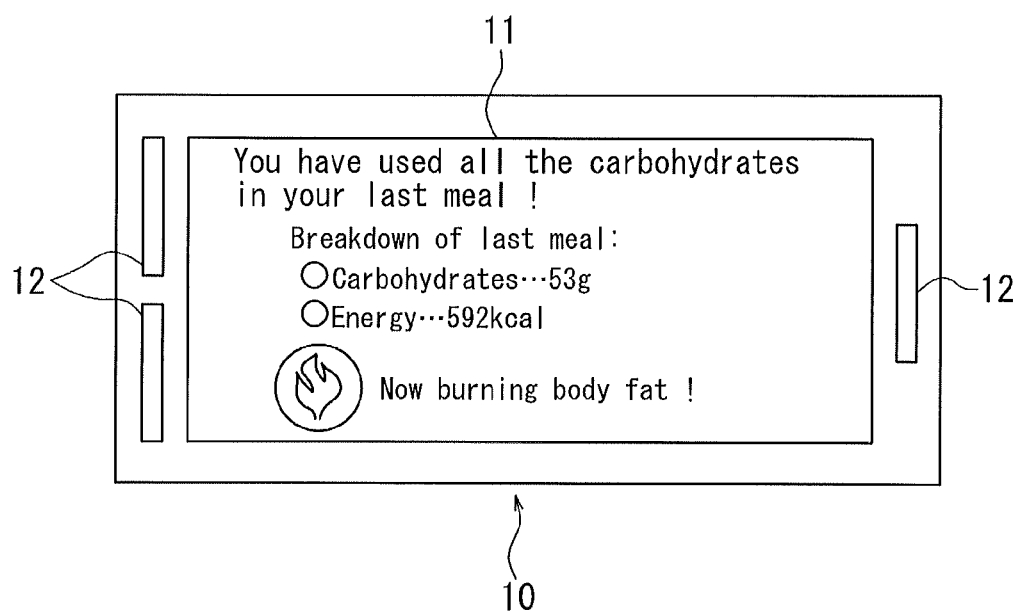
FIG. 3 is a front view of the energy consumption estimator illustrating a state in which the carbohydrate energy in recently ingested food is being displayed.

When it is determined that the energy consumption derived from carbohydrates calculated by the second calculation unit 19 is equivalent to the carbohydrate energy in food ingested near the reset time, the energy consumption derived from carbohydrates calculated by the second calculation unit 19 is displayed on the display 11 as the carbohydrate energy in recently ingested food, for example as illustrated in FIG. 3.

The following briefly describes how the energy consumption derived from carbohydrates calculated by the second calculation unit 19 can be considered equivalent to the carbohydrate energy in food ingested near the reset time. Carbohydrates, and fats and lipids are known to be the sources of energy for activity by the human body. In other words, the total energy consumption by the human body is the sum of energy consumption derived from carbohydrates and energy consumption derived from fats and lipids.

Food typically includes carbohydrates, and fats and lipids. In a regular activity cycle, consumption derived from fats and lipids rapidly decreases after a meal, with consumption of carbohydrates taking priority. When the ingested carbohydrates are almost completely consumed, with only a trace amount thereof remaining stored in the body, consumption of ingested fats and lipids and of fats and lipids stored in the body begins.

Subsequently, the consumption of fats and lipids takes priority until the next time food is ingested, except for special circumstances in which carbohydrates in the body are used, such as during vigorous anaerobic exercise. Accordingly, the energy consumption derived from fats and lipids calculated by the fourth calculation unit 21 based on the amount of acetone is the energy consumption derived from fats and lipids that has been consumed by the body between the end of the most recent meal and the time of detection.

If the total energy consumption was reset near the most recent meal, the total energy consumption calculated by the first calculation unit 18 is the total energy consumption by the body between the end of the most recent meal and the time of detection. Therefore, the energy consumption derived from carbohydrates that have been consumed by the body from after the most recent meal until the time of detection is calculated by subtracting the energy consumption derived from fats and lipids calculated by the fourth calculation unit 21 from the total energy consumption by the body between the end of the most recent meal and the time of detection.

As described above, when the body ingests food, consumption of carbohydrates included in the food takes priority until the carbohydrates have been nearly consumed. Therefore, when carbohydrates other than those for storage in the body have been completely consumed, the energy consumption derived from carbohydrates that the body has consumed between the end of the most recent meal and the time of detection is substantially equal to the carbohydrate energy included in recently ingested food.

Based on the above-described principal, when the energy consumption estimator 10 determines that carbohydrates other than those for storage in the body have been completely consumed, the energy consumption derived from carbohydrates calculated by second calculation unit 19 is displayed as the carbohydrate energy included in recently ingested food. On the other hand, when the energy consumption estimator 10 determines that carbohydrates other than those for storage in the body have not been completely consumed, the energy consumption derived from carbohydrates calculated by second calculation unit 19 is displayed as energy consumption derived from carbohydrates.

Note that the energy consumption estimator 10 determines that carbohydrates other than those for storage in the body have been completely consumed when the energy consumption derived from fats and lipids newly calculated by the fourth calculation unit 21 exceeds the energy consumption derived from fats and lipids before a meal stored in the second storage unit 15.

Note also that after determining that carbohydrates other than those for storage in the body have been completely consumed, upon detection of input indicating calculation of the total energy in ingested food, the third calculation unit 20 calculates the total energy in recently ingested food based on the energy consumption derived from carbohydrates calculated by the second calculation unit 19. The calculated total energy is displayed on the display 11.

Figure 4:
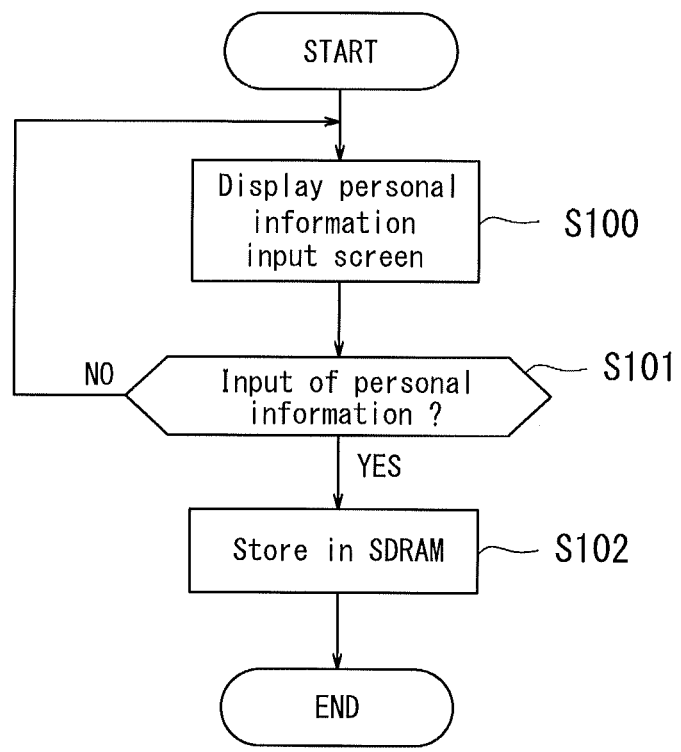
FIG. 4 is a flowchart of information input processing performed by the control unit in the setting mode in Embodiment 1.

Next, in Embodiment 1, information input processing performed by the control unit 23 in the setting mode is described with reference to the flowchart in FIG. 4. The information input processing begins when the input unit 16 detects user input to switch to the setting mode.

In step S100, the control unit 23 displays the personal information input image on the display 11. Upon display of the personal information input image, processing proceeds to step S101.

In step S101, the control unit 23 determines whether the input unit 16 has detected input of personal information by the user. When input of personal information has not been detected, processing returns to step S100, and steps S100 and S101 are repeated until detection of personal information. When input of personal information is detected, processing proceeds to step S102.

In step S102, the control unit 23 records the user's personal information detected by the input unit 16 in the second storage unit 15. After recording of personal information in the second storage unit 15, information input processing terminates.

Figure 5:
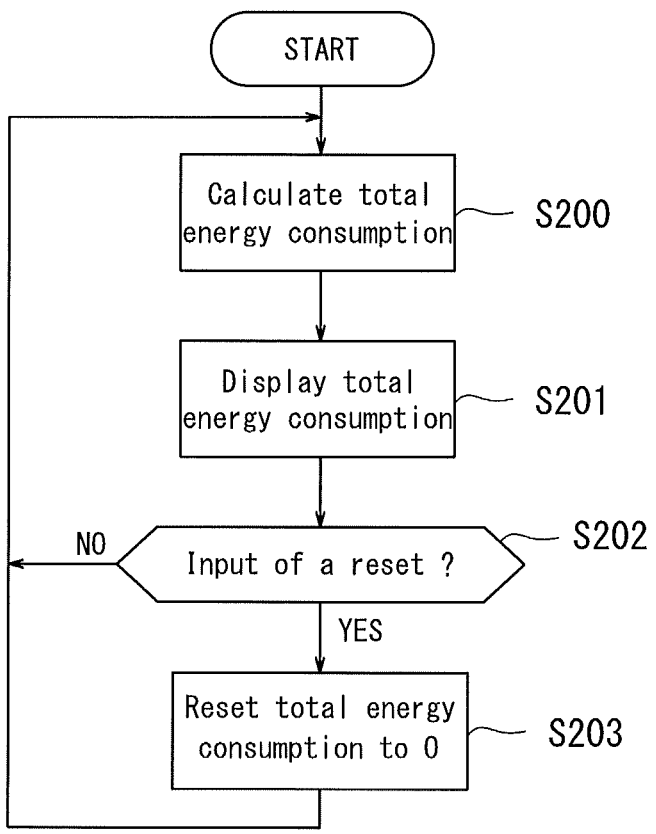
FIG. 5 is a flowchart of total energy consumption calculation processing performed by the control unit in the measurement mode in Embodiment 1.

Next, in Embodiment 1, total energy consumption calculation processing performed by the control unit 23 in the measurement mode is described with reference to the flowchart in FIG. 5. The total energy consumption calculation processing begins when the input unit 16 detects user input to switch to the measurement mode and terminates when power to the energy consumption estimator 10 is turned off after the start of measurement mode.

In step S200, the control unit 23 transmits the acceleration detected by the body motion sensor 17 to the first calculation unit 18. Next, the control unit 23 transmits the user's personal information stored in the second storage unit 15 to the first calculation unit 18. Furthermore, the control unit 23 causes the first calculation unit 18 to calculate the user's total energy consumption. The control unit 23 stores the calculated total energy consumption in the second storage unit 15 in association with the point in time measured by the timer 22. After calculation of the total energy consumption, processing proceeds to step S201.

In step S201, the control unit 23 displays the total energy consumption calculated in step S200 on the display 11. After display of the total energy consumption, processing proceeds to step S202.

In step S202, the control unit 23 determines whether the input unit 16 has detected input of a reset. When input of a reset has not been detected, processing returns to step S200. When input of a reset has been detected, processing proceeds to step S203.

In step S203, the control unit 23 resets the total energy consumption detected by the first calculation unit 18 to zero. After the total energy consumption is reset, processing proceeds to step S200.

Figure 6:
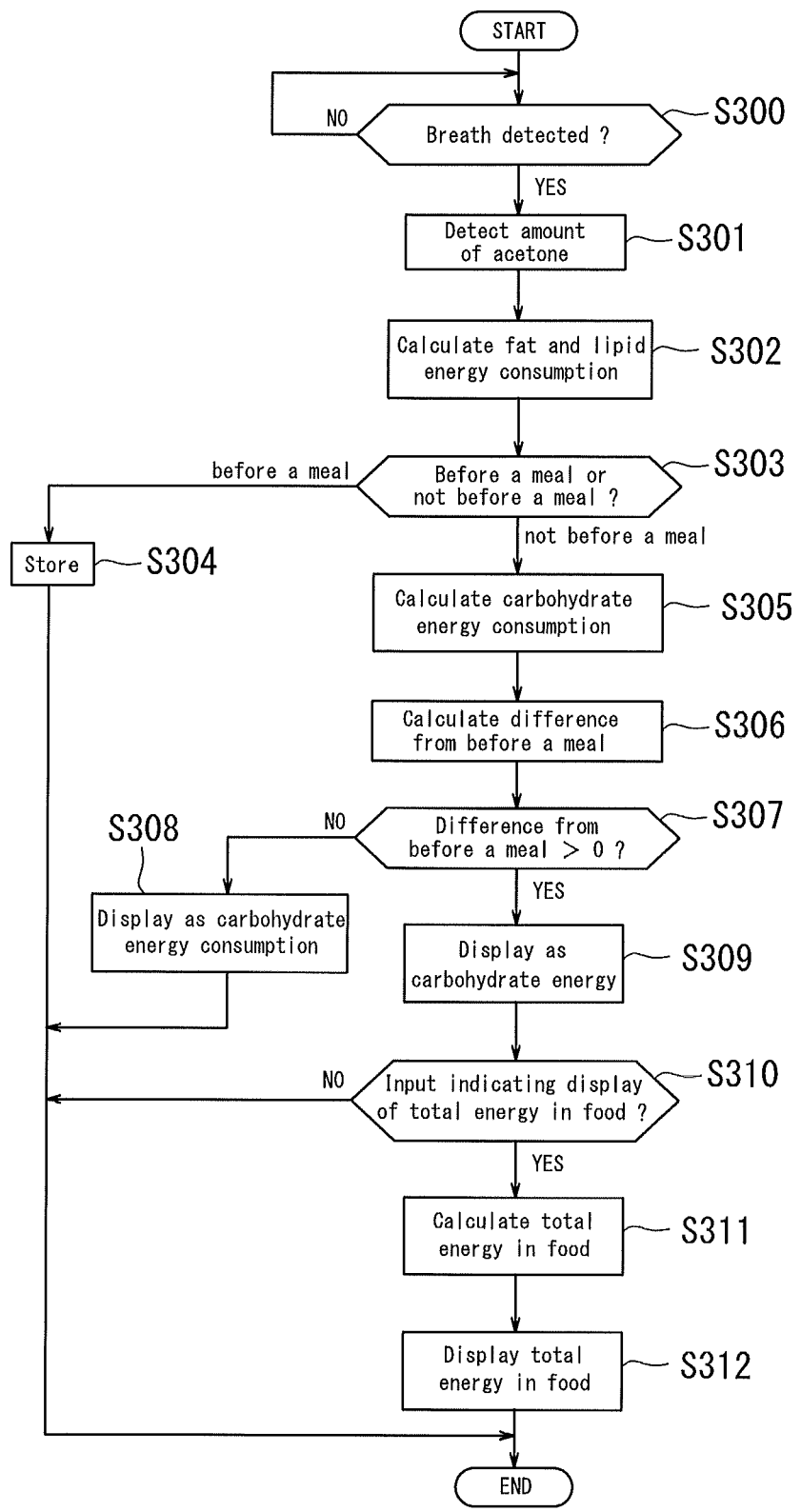
FIG. 6 is a flowchart of energy consumption calculation processing performed by the control unit in the measurement mode in Embodiment 1.

Next, energy consumption calculation processing performed by the control unit 23 in the measurement mode in Embodiment 1 is described with reference to the flowchart in FIG. 6. The energy consumption calculation processing in Embodiment 1 begins when the input unit 16 detects user input indicating fat and lipid consumption measurement during operation in the measurement mode.

In step S300, the control unit 23 determines whether the acetone measurement unit 13 detects breath. Detection of breath is, for example, based on variation in pressure or the like. When breath is not detected, processing enters a standby state while repeating step S300. When breath is detected, processing proceeds to step S301.

In step S301, the control unit 23 causes the acetone measurement unit 13 to detect the amount of acetone. Furthermore, the control unit 23 transmits the detected amount of acetone to the fourth calculation unit 21. After transmission of the amount of acetone, processing proceeds to step S302.

In step S302, the control unit 23 calculates the energy consumption derived from fats and lipids based on the amount of acetone transmitted in step S301. After calculation of the energy consumption derived from fats and lipids, processing proceeds to step S303.

In step S303, the control unit 23 determines whether input detected by the input unit 16 designates that measurement is before a meal or not before a meal. If measurement is before a meal, processing proceeds to step S304. If measurement is not before a meal, processing proceeds to step S305.

In step S304, the control unit 23 stores the energy consumption derived from fats and lipids measured in step S302 in the second storage unit 15, after which energy consumption calculation processing terminates.

In step S305, the control unit 23 transmits the total energy consumption calculated by the first calculation unit 18 and the energy consumption derived from fats and lipids calculated by the fourth calculation unit 21 in step S302 to the second calculation unit 19. Furthermore, the control unit 23 causes the second calculation unit 19 to calculate the energy consumption derived from carbohydrates by subtracting the energy consumption derived from fats and lipids from the total energy consumption. After calculation of the energy consumption derived from carbohydrates, processing proceeds to step S306.

In step S306, the control unit 23 calculates the difference in energy consumption derived from fats and lipids before a meal and not before a meal by subtracting the energy consumption derived from fats and lipids stored in the second storage unit 15 from the energy consumption derived from fats and lipids measured in step S302. After calculation of this difference, processing proceeds to step S307.

In step S307, the control unit 23 determines whether the difference in energy consumption derived from fats and lipids before a meal and not before a meal calculated in step S306 is greater than zero. When the difference is greater than zero, processing proceeds to step S309. When the difference is equal to or less than zero, processing proceeds to step S308.

In step S308, the control unit 23 displays the message "You are still consuming carbohydrate energy in the food you ate", the total energy consumption, and the current energy consumption derived from fats and lipids on the display 11, together with the energy consumption derived from carbohydrates calculated in step S305 as the current energy consumption derived from carbohydrates. After display, energy consumption calculation processing terminates.

In step S309, the control unit 23 displays the energy consumption derived from carbohydrates calculated by the second calculation unit 19 in step S305 on the display 11 as the carbohydrate energy in recently ingested food. After display of the carbohydrate energy, processing proceeds to step S310.

In step S310, the control unit 23 determines whether the input unit 16 has detected input indicating calculation of the total energy in food. When input has not been detected, energy consumption calculation processing terminates. When input has been detected, processing proceeds to step S311.

In step S311, the control unit 23 transmits the carbohydrate energy calculated by the second calculation unit 19 in step S308 and the relationship stored in the first storage unit 14 to the third calculation unit 20. Furthermore, the control unit 23 causes the third calculation unit 20 to calculate the total energy in recently ingested food. After calculation of the total energy, processing proceeds to step S312.

In step S312, the control unit 23 displays the total energy in food calculated by the third calculation unit 20 in step S311 on the display 11. After display of the total energy in food, energy consumption calculation processing terminates.

With the above structure, the energy consumption estimator of Embodiment 1 can calculate the energy consumption derived from carbohydrates consumed by the user.

The energy consumption estimator of Embodiment 1 can also display the calculated energy consumption derived from carbohydrates as the carbohydrate energy in ingested food.

Furthermore, the energy consumption estimator of Embodiment 1 can calculate the total energy in food ingested during a meal based on the energy consumption derived from carbohydrates which was displayed as carbohydrate energy. This allows for extremely easy comprehension of the estimated value of the total energy in ingested food.

Next, Embodiment 2 of the present invention is described. In Embodiment 2, the method of acquiring the energy consumption derived from fats and lipids differs from Embodiment 1. The following describes Embodiment 2, focusing on the differences from Embodiment 1. Note that the same reference signs are used for components having the same structure and functions as in Embodiment 1.

Figure 7:
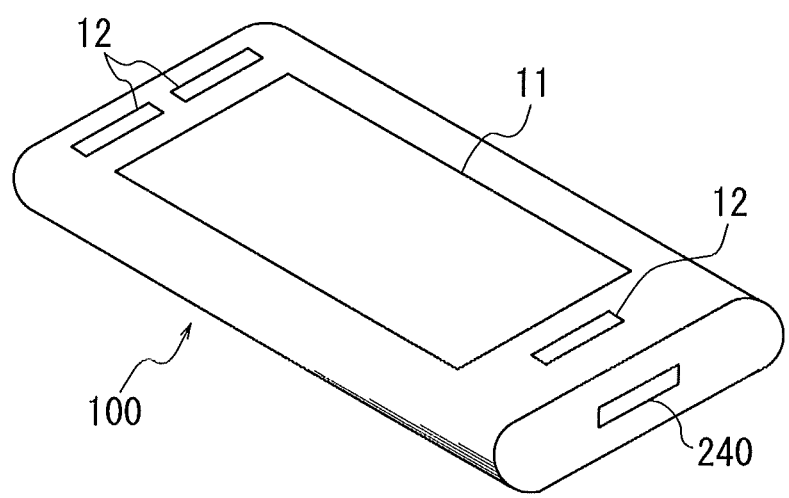
FIG. 7 is an external perspective view of an energy consumption estimator according to Embodiment 2 of the present invention.

As shown in FIG. 7, an energy consumption estimator 100 according to Embodiment 2 is provided with a display 11 and a plurality of buttons 12 as in Embodiment 1. Unlike Embodiment 1, however, an acquisition unit 240 (claimed fat energy consumption acquisition circuitry) is provided on the side of the energy consumption estimator 100. The structure and functions of the display 11 and the plurality of buttons 12 are the same as in Embodiment 1.

The acquisition unit 240 is, for example, a wired or wireless data receiver and receives a variety of data from an external device. For example, from a fat and lipid consumption detector (acetone detector) that detects the amount of acetone included in a user's breath and calculates the user's energy consumption derived from fats and lipids based on the detected amount of acetone, the acquisition unit 240 acquires the user's energy consumption derived from fats and lipids along with the time of detection of the amount of acetone.

Figure 8:
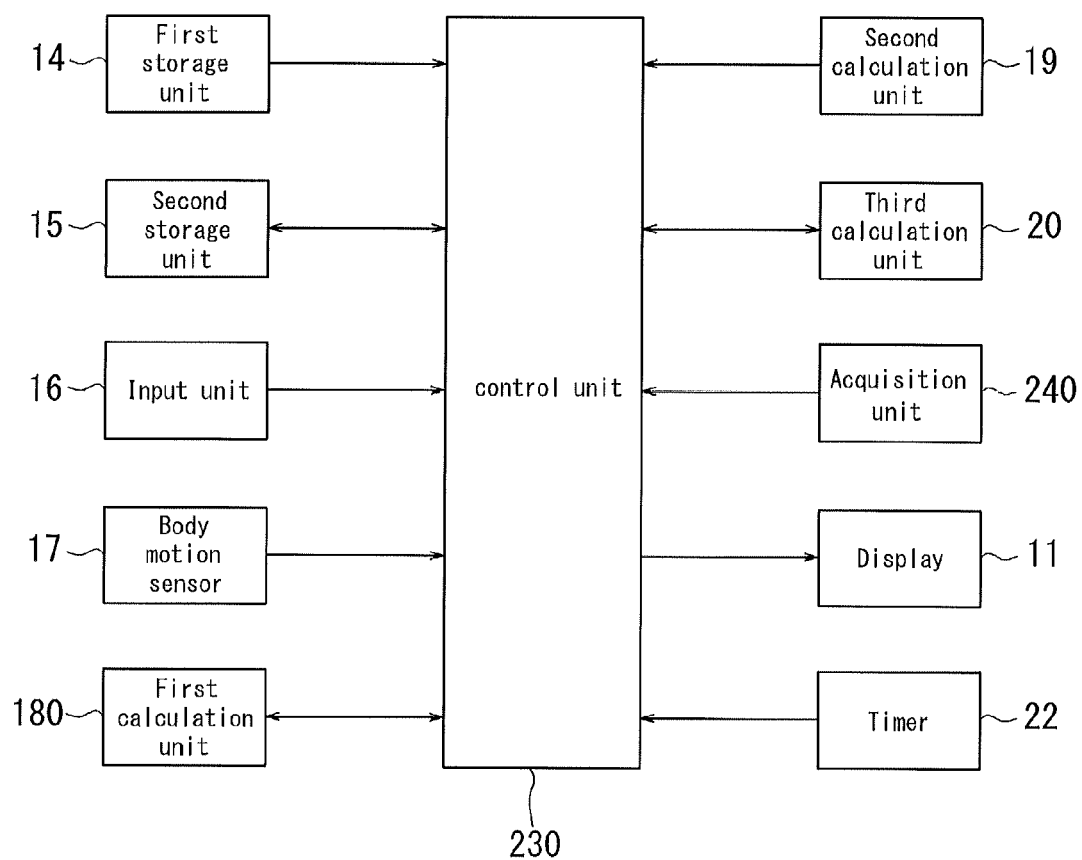
FIG. 8 is a functional block diagram schematically illustrating the internal structure of the energy consumption estimator in FIG. 7.

Next, the internal structure of the energy consumption estimator 100 is described with reference to the functional block diagram in FIG. 8. The energy consumption estimator 100 includes a first storage unit 14, a second storage unit 15, an input unit 16, a body motion sensor 17, a first calculation unit 180, a second calculation unit 19, a third calculation unit 20, the display 11, a timer 22, a control unit 230, and the acquisition unit 240. The structure and functions of the first storage unit 14, the second storage unit 15, the input unit 16, the body motion sensor 17, the second calculation unit 19, the third calculation unit 20, the display 11, and the timer 22 are the same as in Embodiment 1.

As in Embodiment 1, the first calculation unit 180 calculates the user's total energy consumption based on the user's personal information read from the second storage unit 15 and on acceleration in three directions detected by the body motion sensor 17.

Unlike Embodiment 1, the first calculation unit 180 calculates the user's total energy consumption during a specified time period, as described below.

From the fat and lipid consumption detector, the acquisition unit 240 acquires the user's energy consumption derived from fats and lipids along with the time of detection of the amount of acetone, as described above.

The control unit 230 controls the exchange of information between, and the transmission of instructions to, the first storage unit 14, the second storage unit 15, the input unit 16, the body motion sensor 17, the first calculation unit 180, the second calculation unit 19, the third calculation unit 20, the display 11, the timer 22, and the acquisition unit 240, as well as operations by these components.

Next, the functions executed in each of the operation modes of the energy consumption estimator 100 are described in detail. As in Embodiment 1, the operation modes of the energy consumption estimator 100 are a setting mode and a measurement mode.

Input of the user's personal information in the setting mode of the energy consumption estimator 100 is the same as in Embodiment 1.

Calculation of the user's total energy consumption in the measurement mode of the energy consumption estimator 100 is also the same as in Embodiment 1.

In the measurement mode, the energy consumption estimator 100 can acquire the user's energy consumption derived from fats and lipids from the fat and lipid consumption detector. Upon detecting input indicating acquisition of energy consumption derived from fats and lipids during operation in the measurement mode, the energy consumption estimator 100 acquires the energy consumption derived from fats and lipids along with the time of detection of the amount of acetone from the fat and lipid consumption detector.

As in Embodiment 1, upon acquisition of the energy consumption derived from fats and lipids, an image requesting selection of whether detection is before a meal or not before a meal is displayed on the display 11. Also as in Embodiment 1, upon detection of input selecting detection before a meal, the acquired energy consumption derived from fats and lipids is stored in the second storage unit 15 as the energy consumption derived from fats and lipids before a meal.

Unlike Embodiment 1, upon detection of input selecting detection not before a meal, a message requesting input of the time of the most recent meal is displayed on the display 11. When the input unit 16 detects input of the time of the most recent meal, the first calculation unit 180 reads, from the second storage unit 15, the total energy consumption calculated at the point in time closest to the input time (hereinafter referred to as the "initial reference time"). The first calculation unit 180 also reads, from the second storage unit 15, the total energy consumption calculated at the point in time closest to the time of detection of the amount of acetone acquired from the fat and lipid consumption detector (hereinafter referred to as the "measurement reference time"). By calculating the difference between these times, the first calculation unit 180 calculates the user's total energy consumption from the initial reference time until the measurement reference time. Once the total energy consumption from the initial reference time until the measurement reference time is calculated, the second calculation unit 19 calculates the energy consumption derived from carbohydrates as in Embodiment 1 by subtracting the energy consumption derived from fats and lipids acquired by the acquisition unit 240 from the total energy consumption calculated by the first calculation unit 180.

Furthermore, as in Embodiment 1, upon detection of input selecting detection that is not before a meal, it is determined whether the energy consumption derived from carbohydrates calculated by the second calculation unit 19 is equivalent to the carbohydrate energy in food ingested near the time, input into the input unit 16, of the most recent meal. Subsequently, as in Embodiment 1, the total energy derived from carbohydrates calculated by the second calculation unit 19 is displayed on the display 11 as energy consumption derived from carbohydrates for a user who is currently burning carbohydrates, or as the carbohydrate energy in recently ingested food, Furthermore, as in Embodiment 1, the energy consumption estimator 100 calculates the total energy in recently ingested food and displays this value on the display 11.

Next, processes executed by the control unit 230 are described. Note that since the information input processing executed by the control unit 230 in the setting mode is the same as in Embodiment 1, an explanation thereof is omitted. Furthermore, since the total energy consumption calculation processing executed by the control unit 230 in the measurement mode is the same as in Embodiment 1, an explanation thereof is omitted.

Figure 9:
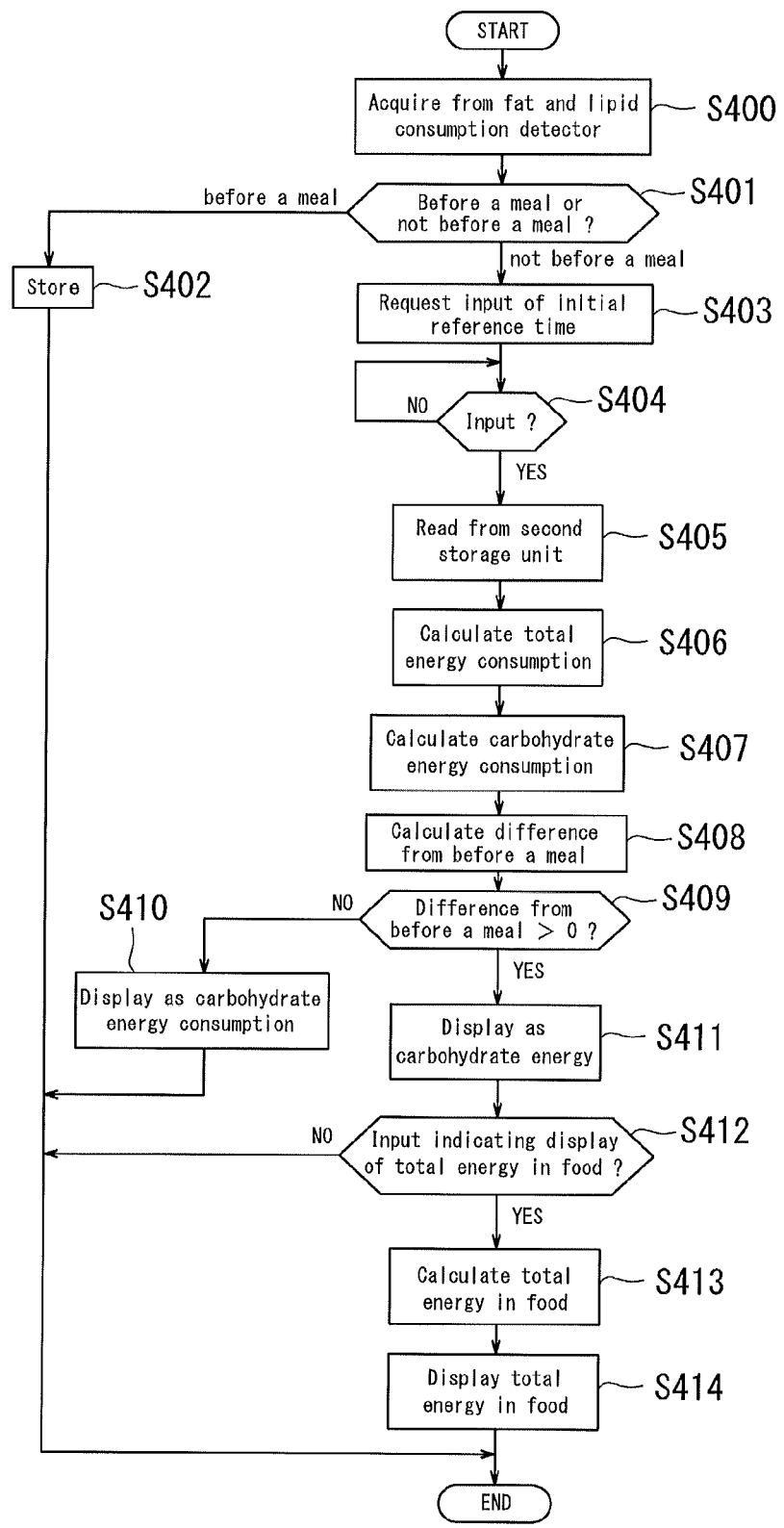
FIG. 9 is a flowchart of energy consumption calculation processing performed by the control unit in the measurement mode in Embodiment 2.

The following describes energy consumption calculation processing performed by the control unit 230 in the measurement mode in Embodiment 2 with reference to the flowchart in FIG. 9. The energy consumption calculation processing in Embodiment 2 also begins when the input unit 16 detects user input indicating fat and lipid consumption measurement during operation in the measurement mode.

In step S400, the control unit 230 acquires the user's energy consumption derived from fats and lipids along with the time of detection of the amount of acetone from the fat and lipid consumption detector. After this acquisition, processing proceeds to step S401.

In steps S401 and S402, the control unit 230 executes the same control as in steps S303 and S304 of the energy consumption calculation processing in Embodiment 1.

In step S403, the control unit 230 displays an image on the display 11 requesting input of the time of the most recent meal. When input has been requested, processing proceeds to step S404.

In step S404, the control unit 230 determines whether the input unit 16 has detected input of the time of the most recent meal. When input has not been detected, processing returns to step S404 and enters a standby state. When input is detected, processing proceeds to step S405.

In step S405, the control unit 230 reads, from the second storage unit 15, the total energy consumption at the point in time closest to the time input in step S407, i.e. at the initial reference time, and transmits this value to the first calculation unit 180. The control unit 230 also reads, from the second storage unit 15, the total energy consumption at the point in time closest to the time of detection of the amount of acetone acquired in step S400, i.e. at the measurement reference time, and transmits this value to the first calculation unit 180. Upon reading of the total energy consumption from the second storage unit 15, processing proceeds to step S406.

In step S406, the control unit 230 causes the first calculation unit 180 to calculate the total energy consumption from the initial reference time to the measurement reference time. After calculation of the total energy consumption, processing proceeds to step S407.

In steps S407 through S414, the control unit 230 executes the same control as in steps S305 through S312 of the energy consumption calculation processing in Embodiment 1.

With the above structure, the energy consumption estimator of Embodiment 2 as well can calculate the energy consumption derived from carbohydrates consumed by the user. Furthermore, the energy consumption estimator of Embodiment 2 as well can display the calculated energy consumption derived from carbohydrates as the carbohydrate energy in ingested food. Moreover, the energy consumption estimator of Embodiment 2 as well can calculate the total energy in food ingested during a meal based on the energy consumption derived from carbohydrates which was displayed as carbohydrate energy.

Although the present invention has been described by way of examples with reference to the accompanying drawings, it is to be noted that various changes and modifications will be apparent to those skilled in the art. Therefore, such changes and modifications are to be understood as included within the scope of the present invention.

For example, in Embodiments 1 and 2, the first calculation units 18 and 180 calculate the total energy consumption based on acceleration in three directions detected by the body motion sensor 17. Alternatively, however, the total energy consumption may be acquired from a measurement device having a body motion sensor and a first calculation unit. Furthermore, a history of acceleration in three directions may be acquired from a measurement device having a body motion sensor, and the total energy consumption may be calculated based on the acquired acceleration in three directions.

In Embodiments 1 and 2, the energy consumption derived from carbohydrates is calculated each time the energy consumption derived from fats and lipids is calculated, even after carbohydrates have been completely consumed. Alternatively, however, it is possible to perform this calculation only once. When carbohydrates have been completely consumed, the energy consumption derived from carbohydrates is considered to be constant, regardless of the time at which the energy consumption derived from fats and lipids is calculated. Therefore, when it is determined that carbohydrates have been completely consumed, the energy consumption derived from carbohydrates may be stored in memory, such as the second storage unit 15, and upon subsequent calculation of the energy consumption derived from fats and lipids, the stored energy consumption derived from carbohydrates may be read and displayed.

In Embodiment 1, the energy consumption estimator 10 includes the first calculation unit 18 through the fourth calculation unit 21 as separate units, yet the calculations performed by these units may all be performed by a single calculation unit. Similarly, in Embodiment 2, the energy consumption estimator 100 includes the first calculation unit 180 through the third calculation unit 20 as separate units, yet the calculations performed by these units may all be performed by a single calculation unit.

In Embodiment 2, the acquisition unit 240 acquires the user's energy consumption derived from fats and lipids from the fat and lipid consumption detector, but instead the acquisition unit 240 may acquire an amount of acetone. As in Embodiment 1, the energy consumption estimator 100 can calculate the energy consumption derived from fats and lipids based on the acquired amount of acetone.

REFERENCE SIGNS LIST 10, 100: Energy consumption estimator
11: Display
12: Button
13: Acetone measurement unit
14: First storage unit
15: Second storage unit
16: Input unit
17: Body motion sensor
18, 180: First calculation unit
19: Second calculation unit
20: Third calculation unit
21: Fourth calculation unit
22: Timer
23: Control unit
240: Acquisition unit

The invention claimed is:

1. An energy consumption estimator comprising:
a total energy consumption acquisition circuitry configured to acquire a total energy consumption for a user;
a fat energy consumption acquisition circuitry configured to acquire an energy consumption derived from fats for the user;
a carbohydrate energy calculation circuitry configured to calculate an energy consumption derived from carbohydrates for the user based on the total energy consumption acquired by the total energy consumption acquisition circuitry and the energy consumption derived from fats acquired by the fat energy consumption acquisition circuitry;
a comparison circuitry configured to compare a first energy consumption acquired by the fat energy consumption acquisition circuitry before a most recent meal with a second energy consumption newly acquired by the fat energy consumption acquisition circuitry; and
wherein when the second energy consumption is greater than the first energy consumption, the comparison circuitry determines the energy consumption derived from carbohydrates calculated by the carbohydrate energy calculation circuitry as carbohydrate energy in the most recent meal, and
the fat energy consumption acquisition circuitry includes an acetone detection circuitry configured to detect an amount of acetone released by the user and a fat energy consumption calculation circuitry configured to calculate the energy consumption derived from fats for the user based on the amount of acetone detected by the acetone detection circuitry.

2. The energy consumption estimator of claim 1, further comprising:
a first storage circuitry configured to store a relationship between total energy in food and energy consumption derived from carbohydrates; and
a total energy calculation circuitry configured to calculate a total energy in food ingested by the user based on the energy consumption derived from carbohydrates calculated by the carbohydrate energy calculation circuitry and on the relationship stored in the first storage circuitry.

3. The energy consumption estimator of claim 1, wherein the fat energy consumption acquisition circuitry acquires the energy consumption derived from fats for the user from an acetone detector that detects an amount of acetone released by the user and that calculates the energy consumption derived from fats for the user based on the detected amount of acetone.

4. The energy consumption estimator of claim 1, wherein when the second energy consumption is equal to or less than the first energy consumption, the comparison circuitry determines the energy consumption derived from carbohydrates calculated by the carbohydrate energy calculation circuitry as a current energy consumption derived from carbohydrates.

5. The energy consumption estimator of claim 1, further comprising:
a display for displaying an output from the total energy consumption acquisition circuitry, the fat energy consumption acquisition circuitry, the carbohydrate energy calculation circuitry, and the comparison circuitry.

6. The energy consumption estimator of claim 1, wherein based on the total energy consumption from an initial reference time until a measurement reference time, the carbohydrate energy calculation circuitry calculates the energy consumption derived from carbohydrates ingested by the user near the initial reference time.

7. The energy consumption estimator of claim 6, further comprising:
   an input circuitry configured to detect input of a reset of the total energy consumption acquired by the total energy consumption acquisition circuitry, wherein
   the carbohydrate energy calculation circuitry uses the total energy consumption calculated after detecting the input of the reset as the total energy consumption from the initial reference time until the measurement reference time.

8. The energy consumption estimator of claim 6, further comprising:
   a timer configured to measure time;
   a second storage circuitry configured to store the total energy consumption acquired by the total energy consumption acquisition circuitry in association with the time measured by the timer; and
   an input circuitry configured to detect input of the initial reference time and the measurement reference time, wherein
   the total energy consumption acquisition circuitry reads the total energy consumption at the initial reference time detected by the input circuitry from the second storage circuitry, acquires the total energy consumption at the measurement reference time, and calculates the total energy consumption from the initial reference time until the measurement reference time by subtracting the total energy consumption at the initial reference time from the total energy consumption at the measurement reference time.

9. The energy consumption estimator of claim 8, wherein the fat energy acquisition circuitry acquires, from an acetone detector that detects an amount of acetone released by the user, the amount of acetone of the user and calculates the energy consumption derived from fats for the user based on the acquired amount of acetone.

10. An energy consumption estimator comprising:
    a total energy consumption acquisition circuitry configured to acquire a total energy consumption for a user;
    a fat energy consumption acquisition circuitry configured to acquire an energy consumption derived from fats for the user;
    a carbohydrate energy calculation circuitry configured to calculate an energy consumption derived from carbohydrates for the user based on the total energy consumption acquired by the total energy consumption acquisition circuitry and the energy consumption derived from fats acquired by the fat energy consumption acquisition circuitry;
    a comparison circuitry configured to compare a first energy consumption acquired by the fat energy consumption acquisition circuitry before a most recent meal with a second energy consumption newly acquired by the fat energy consumption acquisition circuitry;
    wherein when the second energy consumption is greater than the first energy consumption, the comparison circuitry determines the energy consumption derived from carbohydrates calculated by the carbohydrate energy calculation circuitry as carbohydrate energy in the most recent meal; and
    the total energy consumption acquisition circuitry includes a tri-axis acceleration sensor module configured to detect acceleration of the energy consumption estimator in three orthogonal directions and a total energy consumption calculation circuitry configured to calculate the total energy consumption for the user based on the acceleration detected by the tri-axis acceleration sensor module.

* * * * *